US00RE37768E

(19) United States
(12) Reissued Patent
Brodeur et al.

(10) Patent Number: US RE37,768 E
(45) Date of Reissued Patent: Jun. 25, 2002

(54) **DNA ENCODING THE 15 KD OUTER MEMBRANE PROTEIN OF *HAEMOPHILUS INFLUENZAE***

(76) Inventors: Bernard R. Brodeur; Josee Hamel, both of 2401 Maritain, Sillery, Quebec (CA), G1T 1N6; Robert S. Munson, Jr., 4825 Canterwood Ct., Hilliard, OH (US) 43026; Susan Grass, 4555 Southridge Pines Dr., St Louis, MO (US) 63128

(21) Appl. No.: 09/053,945

(22) Filed: Apr. 2, 1998

Related U.S. Patent Documents

Reissue of:
(64) Patent No.: 5,503,992
Issued: Apr. 2, 1996
Appl. No.: 08/061,314
Filed: Sep. 7, 1993

(51) Int. Cl.[7] ..... A61K 39/02; A61K 39/102; C07H 21/02; C12P 21/06

(52) U.S. Cl. ..... 435/69.3; 536/22.1; 536/23.1; 536/23.7; 530/300; 424/184.1; 424/185.1; 424/256.1; 424/200.1; 435/6; 435/320.1; 435/252.2

(58) Field of Search ..... 435/69.3, 6, 320.1, 435/252.2, 252.8, 252.3; 536/22.1, 23.1, 23.7; 530/300; 424/184.1, 185.1, 256.1, 200.1

(56) References Cited

PUBLICATIONS

Young et al. PNAS. 80: 1194–1198. 1993.*
Dugourd et al. Abstracts of Gen Meet ASM p. 88, Abstract B–373.*
Green et al. Infection and Immunity 55: 2878–2883, 1987.*
Grass et al., Abstracts of Gen Meeting of ASM P. 105, Abst. D–57.*
Humel et al. J. Med. Microbiol. 23: 163–70, 1987, Abstract only.*

* cited by examiner

*Primary Examiner*—Jennifer E. Graser
(74) *Attorney, Agent, or Firm*—Foley & Lardner

(57) ABSTRACT

Murine monoclonal antibodies directed against a novel outer membrane protein (OMP) of Haemophilus influenzae have been isolated and characterized. The gene encoding of the outer membrane protein has also been isolated and characterized. Portions of the DNA sequence of the 15 kD OMP gene are useful as probes to diagnose the presence of Haemophilus influenzae in samples. These DNA's also make available polypeptide sequences of immunoreactive epitopes encoded within the gene, thus permitting the production of polypeptides which are useful as standards or reagents in diagnostic tests and/or as components of vaccines. Monoclonal antibodies directed against epitopes of the 15 kD OMP are also useful for diagnostic tests and as therapeutic agents for passive immunization.

21 Claims, 4 Drawing Sheets

```
        10        20        30        40        50        60
GATCCCACCTTGTTTATTCCAATAATGGAACTTTATTTTATTAAAGGTATCTAAGTAGCA

        70        80        90       100       110       120
CCCTATATAGGGATTAATTAACGAGGTTTAATAATGAACTTTAACTAAAATTTTACCAGC

       130       140       150       160       170       180
ATTTGCTGCTGTAGTCTGTATTATCTGCTTGTGCAAAGGATGCACCTGAAATGACAAAAT
                                                MetThrLysS

       190       200       210       220       230       240
CATCTGCGCAAATAGCTGAAATGCAAACACTTCCAACAATCACTGATAAAACAGTTGTAT
erSerAlaGlnIleAlaGluMetGlnThrLeuProThrIleThrAspLysThrValValT

       250       260       270       280       290       300
ATTCCTGCAATAAACAAACGGTGACTGCTGTGTATCAATTTGAAAACCAAGAACCAGTTG
yrSerCysAsnLysGlnThrValThrAlaValTyrGlnPheGluAsnGlnGluProValA

       310       320       330       340       350       360
CTGCAATGGTAAGTGTGGGCGATGGCATTATTGCCAAAGATTTTACTCGTGATAAATCAC
laAlaMetValSerValGlyAspGlyIleIleAlaLysAspPheThrArgAspLysSerG

       370       380       390       400       410       420
AAAATGACTTTACAAGTTTCGTTTCTGGGGATTATGTTTGGAATGTAGATAGTGGCTTAA
lnAsnAspPheThrSerPheValSerGlyAspTyrValTrpAsnValAspSerGlyLeuT

       430       440       450       460       470       480
CGTTAGATAAATTTGATTCTGTTGTGCCTGTCAATTTAATTCAAAAAGGTAAATCTAGCG
hrLeuAspLysPheAspSerValValProValAsnLeuIleGlnLysGlyLysSerSerA

       490       500       510       520       530       540
ATAATATCATCGTCAAAAATTGTGATGTAAACGTAAAAGCAACTAAAAAAGCAAATTTAT
spAsnIleIleValLysAsnCysAspValAsnValLysAlaThrLysLysAlaAsnLeu*

       550       560       570       580       590       600
AATTAATCCCAAATGACCAGCATAATTGCTGGTTATTTATCTTCCTCGAGGGGAGATTTT
oc

       610       620       630       640       650       660
TTCTTGA
```

FIG. 5

DNA ENCODING THE 15 KD OUTER MEMBRANE PROTEIN OF *HAEMOPHILUS INFLUENZAE*

Matter enclosed in heavy brackets [ ] appears in the original patent but forms no part of this reissue specification; matter printed in italics indicates the additions made by reissue.

BACKGROUND OF THE INVENTION

1. Field of the Invention

This invention relates to the 15 kD outer membrane protein of Haemophilus influenzae type b and nontypable Haemophilus influenzae.

For the sake of simplicity, Haemophilus influenzae is hereinafter referred to as H. influenzae.

2. Discussion of the Prior Art

Haemophilus influenzae type b is a major cause of meningitis and other invasive bacterial diseases in children under the age of five. Efficacious vaccines have been produced. The vaccines contain the type b capsular polysaccharide conjugated to a carrier protein. Nontypable H. influenzae cause surface mucosal infections in children and adults. Such organisms also cause invasive disease in children in the developing world and immunocompromised patients. The vaccines which have been developed to prevent disease due to type b organisms are not effective against nontypable H. influenzae.

SUMMARY OF THE INVENTION

Outer membrane proteins elicit antibodies which are protective in animal models and therefore should be considered as components in the next generation of vaccines designed to prevent both serotype b and nontypable Haemophilus disease.

The object of the invention is to clone the gene for this H. influenzae protein, and to determine the DNA sequence thereof.

Accordingly, the present invention relates to a recombinant polynucleotide comprising a nucleotide sequence for the 15 kD protein of Haemophilus influenzae type b and nontypable Haemophilus influenzae, said protein having the amino acid sequence as follows:

```
         10        20        30        40        50        60
GATCCCACCTTGTTTATTCCAATAATGGAACTTTATTTTATTAAAGGTATCTAAGTAGCA

         70        80        90       100       110       120
CCCTATATAGGGATTAATTAACGAGGTTTAATAATGAACTTTAACTAAAATTTTACCAGC

        130       140       150       160       170       180
ATTTGCTGCTGTAGTCTGTATTATCTGCTTGTGCAAAGGATGCACCTGAAATGACAAAAT
                                                MetThrLysS

        190       200       210       220       230       240
CATCTGCGCAAATAGCTGAAATGCAAACACTTCCAACAATCACTGATAAAACAGTTGTAT
erSerAlaGlnIleAlaGluMetGlnThrLeuProThrIleThrAspLysThrValValT

        250       260       270       280       290       300
ATTCCTGCAATAAACAAACGGTGACTGCTGTGTATCAATTTGAAAACCAAGAACCAGTTG
yrSerCysAsnLysGlnThrValThrAlaValTyrGlnPheGluAsnGlnGluPrnValA

        310       320       330       340       350       360
CTGCAATGGTAAGTGTGGGCGATGGCATTATTGCCAAAGATTTTACTCGTGATAAATCAC
laAlaMetValSerValGlyAspGlyIleIleAlaLysAspPheThrArgAspLysSerG

        370       380       390       400       410       420
AAAATGACTTTACAAGTTTCGTTTCTGGGGATTATGTTTGGAATGTAGATAGTGGCTTAA
lnAsnAspPheThrSerPheValSerGlyAspTyrValTrpAsnValAspSerGlyLeuT

        430       440       450       460       470       480
CGTTAGATAAATTTGATTCTGTTGTGCCTGTCAATTTAATTCAAAAAGGTAAATCTAGCG
hrLeuAspLysPheAspSerValValProValAsnLeuIleGlnLysGlyLysSerSerA

        490       500       510       520       530       540
ATAATATCATCGTCAAAAATTGTGATGTAAACGTAAAAGCAACTAAAAAAGCAAATTTAT
spAsnIleIleValLysAsnCysAspValAsnValLysAlaThrLysLysAlaAsnLeu*

        550       560       570       580       590       600
AATTAATCCCAAATGAGCAGCATAATTGCTGGTTATTTATCTTCCTCGAGGGGAGATTTT
oc
        610       620       630       640       650       660
TTCTTGA (SEQ ID. NOS: 1 and 2)
```

Nucleotide Sequence Coding for a Common Outer Membrane Protein from H. influenzae and Monoclonal Antibodies The 15 kD outer membrane protein described herein is conserved among type b and nontypable H. influenzae. Epitopes on the native protein are recognized by the murine monoclonal antibodies 6B11, 1A6, and 5E6. The epitopes are present on the surface of intact H. influenzae cells. The gene for the 15 kD protein has been cloned and the DNA sequence thereof has been determined. The gene, when expressed in an appropriate host/vector system, produces a recombinant protein which is reactive with the monoclonal antibodies. Since the protein is antigenically highly conserved, it should receive serious consideration for inclusion in a vaccine to prevent H. influenzae disease. Moreover monoclonal antibodies and DNA probes may be used as a diagnostic tool to detect the presence of H. influenzae.

BRIEF DESCRIPTION OF THE DRAWINGS

FIG. 5 is the amino acid sequence for the polynucleotide of the present invention. (*SEQ ID NOs 1 and 2 are set forth in this Figure.*)

DESCRIPTION OF THE PREFERRED EMBODIMENT GENERATION OF MONOCLONAL ANTIBODIES

Monoclonal antibodies (Mabs) were obtained from two independent fusion experiments. Mab 1A6 was generated from Balb/c mice immunized with sarcosyl-insoluble proteins of nontypable H. influenzae MTL6 as described by Hamel et al [see Journal of General Microbiology (1992), 138, 161–168] and monoclonal antibodies 6B11 and 5E6, were produced from mice immunized with outer membranes extracted from nontypable H. influenzae 12085 by the lithium chloride method described by Hamel et al [see J. Med. Microbiology, (1987) 23 163–170]. Isotype analysis revealed that the 1A6, 6B11 and 5E6 hybridomas secreted immunoglobulin IG2a, IG1 and IG3 respectively.

Figure 1:
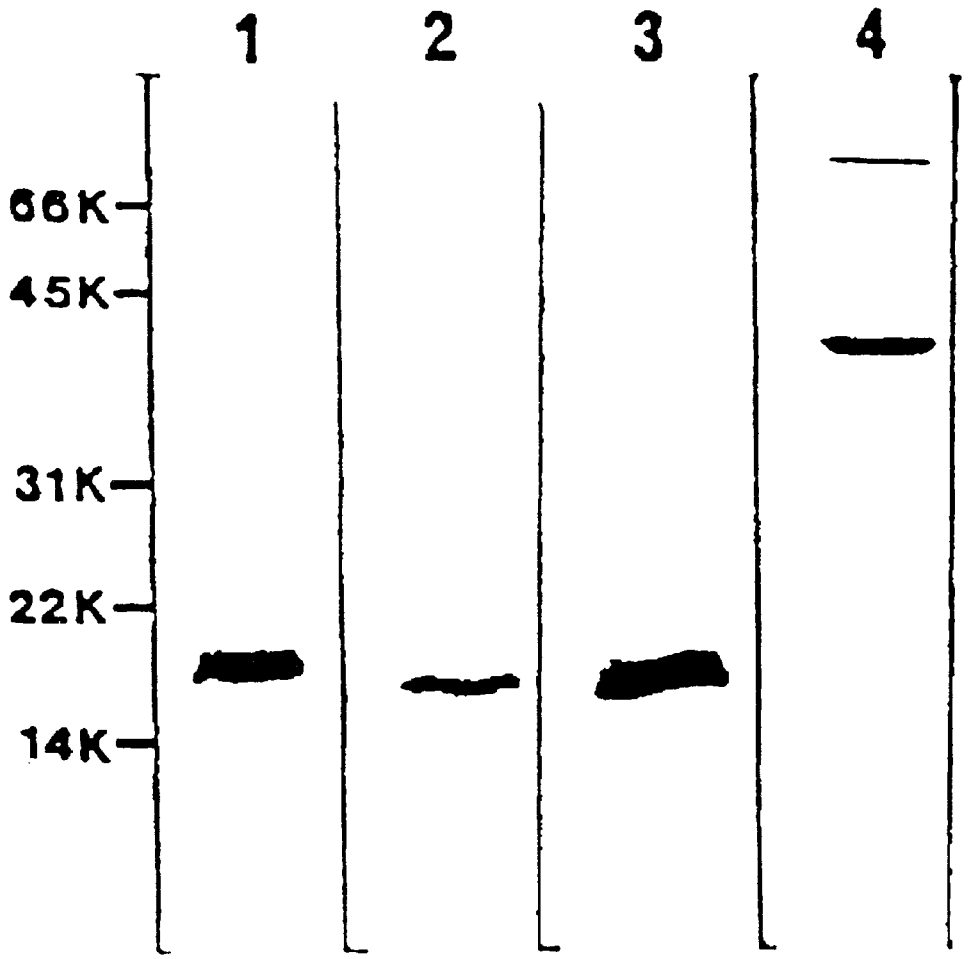
FIG. 1 is a Western blot analysis of H. influenzae with monoclonal antibodies.

Referring to FIG. 1, Western Immunoblotting analysis of outer membrane preparations was performed. Outer membrane preparations were fractionated on 16% SDS-PAGE, transferred to nitrocellulose, and probed with Mab 1A6 (lane 1), 6B11 (lane 2), 5E6 (lane 3) and porin-specific Mab P2-18 (lane 4). The analysis indicated that the monoclonal antibodies were directed against a protein with an apparent mass of 15 kD. Antibody accessibility radioimmunoassay [see Proulx et al, Infection and Immunity (1991)59, 963–970] indicated that monoclonal antibodies bound to surface-exposed epitopes on both type b and nontypable H. influenzae isolates.

CONSERVATION OF 15 KD-EPITOPES

A total of 193 H. influenzae isolates were tested by dot blot immunoassay for their reactivity with monoclonal antibodies 1A6, 6B11 and 5E6.

TABLE 1

Characteristics of *H. influenzae* strains tested for monoclonal antibody reactivities

| Strains | Number Reactive/ Total Number[a] |
|---|---|
| *H. influenzae* serotype b: | |
| Division: Clonal group A1[b] | 27/27 |
| Clonal group A2 | 59/59 |
| Clonal group B1 | 5/5 |
| Division: Clonal group J | 1/1 |
| *H. influenzae* serotype a: | |
| Division 1 | 2/2 |
| Division 2 | 2/2 |
| *H. influenzae* serotype d: | 2/2 |
| Division 1 | |

TABLE 1-continued

Characteristics of *H. influenzae* strains tested for monoclonal antibody reactivities

| Strains | Number Reactive/ Total Number[a] |
|---|---|
| *H. influenzae* nontypable | 95/95 |
| Other gram-negative species[c] | 0/19 |

[a]Reactivity of MAb 6B11. and 5E6 was tested individually by blot immunoassay.
[b]The chromosomal genotypes of *H. influenzae* expressing serotype a, b and d capsule were previously characterized by Dr. James Musser (see J. Musser et al "Global Genetic STructure and Molecular Epidermiology of Encopsulated *Haemophilus Influenzae*. Reviews of Infectious Diseases 12, 75–111).
[c]Nineteen isolates representing 19 other gram-negative species were tested. These are listed in Table 2.

TABLE 2

| Non-*H. influenzae* isolates tested |
|---|
| *Alcaligenes odorans* |
| *Citrobacter freundii* |
| *Flavobacterium odoratum* |
| *Edwardsiella tarda* |
| *Enterobacter cloaca* |
| *Enterobacter aerogenes* |
| *Klebsiella pneumoniae* |
| *Moraxella catharrhalis* |
| *Neisseria lactamica* |
| *Neisseria perflava* |
| *Neisseria subflava* |
| *Pseudomonas aeruginaosa* |
| *Proteus vulgaris* |
| *Providencia rettgeri* |
| *Serratia marcescens* |
| *Salmonella thyphimurium* |
| *Shigella flexneri* |
| *Shigella sonnei* |
| *Xanthomonas maltophilia* |

MOLECULAR CLONING OF THE GENE FOR THE 15 KD OUTER MEMBRANE PROTEIN

Figure 2:
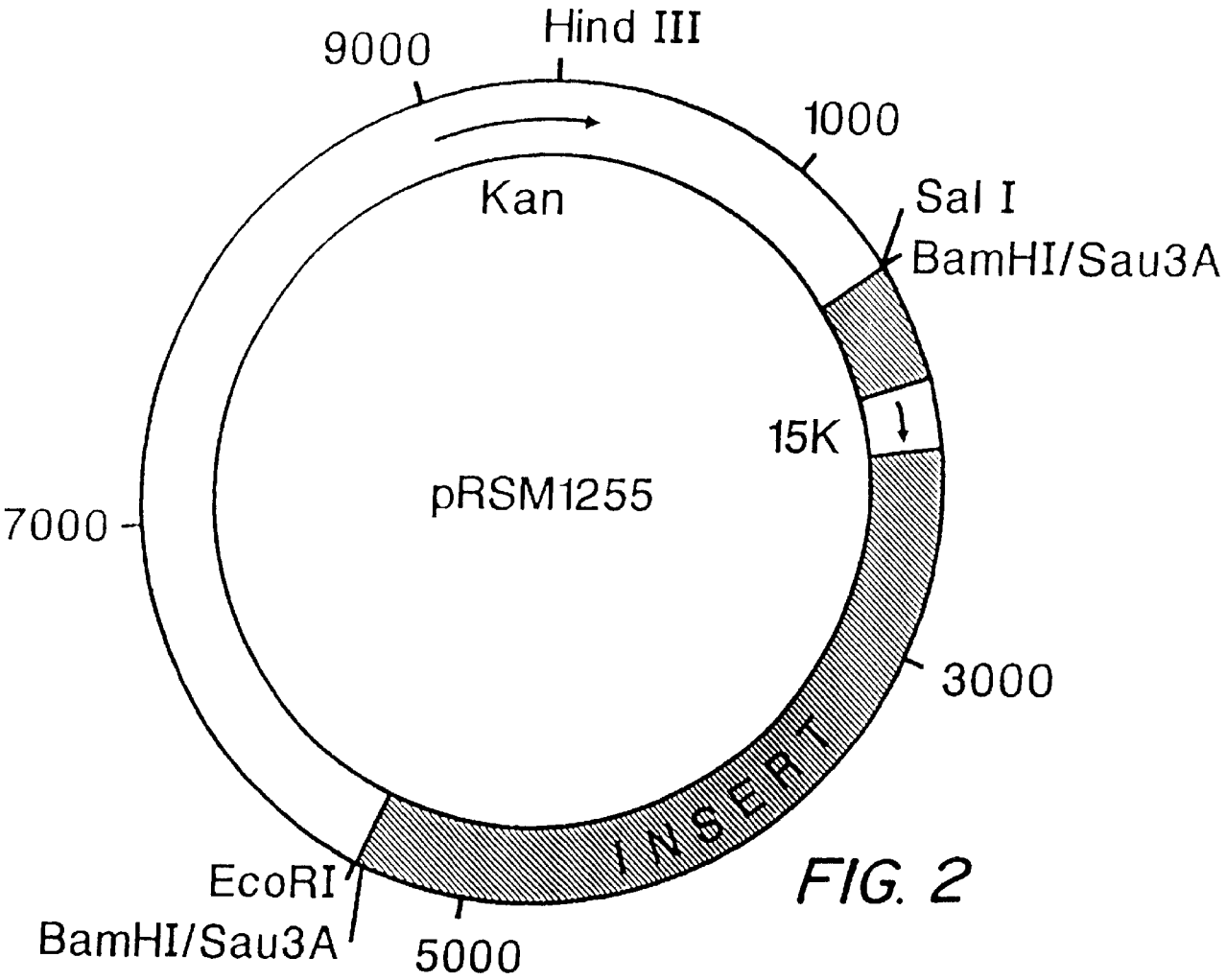
FIG. 2 is a partial restriction map of plasmid pRSM1255 which contains the gene for the 15 kD outer membrane protein from H. influenzae type b strain 1613.
Figure 3:
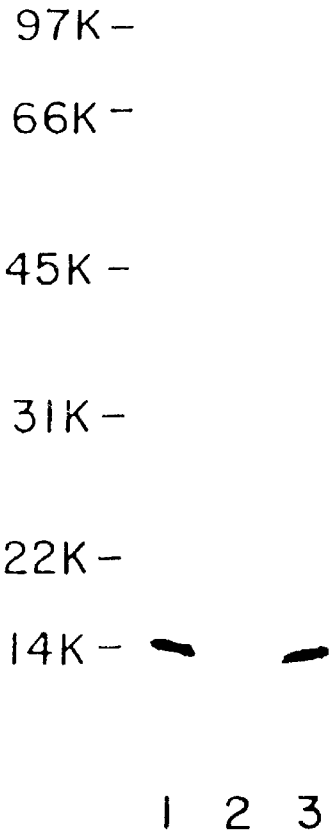
FIG. 3 is a Western blot analysis of the expression of the recombinant 15 kD protein.

A lambda EMBL3 genomic library of DNA from H. influenzae strain 1613 was immunologically screened with murine monoclonal antibody 6B11 as described by Munson and Grass [see Infection and Immunity (1988) 561 2235–2242]. An immunologically reactive clone was isolated by plaque purification. A liquid lysate was prepared and DNA was purified from a Promega lambda DNA kit according to the manufacturer's directions. The Haemophilus insert was identified as a SalI fragment of approximately 16 kb. DNA from the lambda clone was partially digested with Sau3A and fragments of approximately 3–6 kb were isolated by preparative agarose gel electrophoresis. The 3–6 kb fragments were ligated into the low copy number vector pGD103 [see Deich et al, Journal of Bacteriology (1988) 489– 498] which had been digested sequentially with BamHI and alkaline phosphatase. The ligation mixture was transformed into E. coli strain LE392 and the cells were plated on LB agar containing 35 μg/ml of kanamycin. Immunologically reactive colonies were identified by screening with murine Mab 6B11. Strain LE392/pRSM1255 was saved for further study. As shown in FIG. 2 plasmid pRSM1255 has an insert of approximately 3.8 kb. Strain LE392/pRSM1255 produces the full size protein as determined by Western blot (see FIG. 3). Membrane preparations were fractionated by SDS-PAGE, transferred to nitrocellulose and probed with murine monoclonal antibody 6B11. Lane 1is the total membrane preparation of H. influenzae strain 1613; lane 2 is the total membrane preparation of E. coli strain LE392/pGD103 and lane 3 is the total membrane preparation of E. coli strain LE392/pRSM1255. The full size 15 Kd protein is produced by E. coli strain LE392/pRSM1255.

Figure 4:
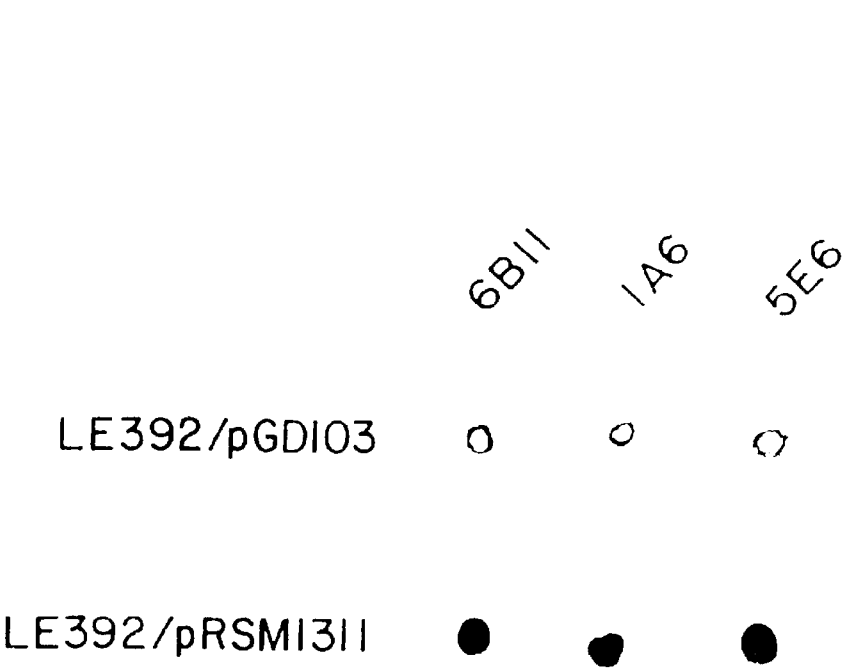
FIG. 4 is a dot blot immunoassay of extracts of E. coli strains LE392/pGD103 and LE392/pRSM1311.

In order to further subclone the gene for sequencing, pRSM1255 was partially digested with Sau3A, fragments of approximately 0.5 to 1.5 kb were isolated, ligated into BamHI-treated pGD103 and transformed into E. coli strain LE392. An immunologically positive clone, designated LE392/pRSM1311 was saved for further analysis. Western blot analysis employing Mab 6B11 indicated that the full size protein was produced by this strain (data not shown). The Haemophilus insert in pRSM1311 is approximately 0.6 kb in size. Extracts of E. coli strain LE392/pRSM1311 react with all three murine Mabs (FIG. 4). 5 $\mu$g of cell extracts were applied to the nitrocellulose and probed with Mabs 3B11, 1A6, and 5E6.

SEQUENCE ANALYSIS

The insert was cloned into M13mp18 and M13mp19 as a SalI to EcoRI fragment and sequenced in both directions. A 369 codon open reading frame (*SEQ ID NO:3*) was identified encoding a protein composed of 123 amino acids (*SEQ ID NO:2*) and having a molecular weight of 13,460. The open reading frame is notable for a lysine at position 3 and a cysteine at position 26 suggesting that the protein is a lipoprotein with a 25 amino acid leader peptide. (*The sequence of the protein without the leader peptide is set forth in SEQ ID NO:4.*)

DNA and protein sequence analysis were done using Gen Bank (a trademark of NIH) and EMBL (from European Molecular Biology Organization) data bases. The nucleotide (*SEQ ID NO:1*) and derived amino acid sequence (*SEQ ID NO:2*) of the 15 kD outer membrane protein of H. influenzae type b, strain 1613 is set out in Table 3.

TABLE3

MW for gene product = i3460. Number of amino acids = 123

```
         10        20        30        40        50        60
GATCCCACCTTGTTTATTCCAATAATGGAACTTTATTTTATTAAAGGTATCTAAGTAGCA

         70        80        90       100       110       120
CCCTATATAGGGATTAATTAACGAGGTTTAATAATGAACTTTAACTAAAATTTTACCAGC

        130       140       150       160       170       180
ATTTGCTGCTGTAGTCTGTATTATCTGCTTGTGCAAAGGATGCACCTGAAATGACAAAAT
Met ThrLys S
        190       200       210       220       230       240
CATCTGCGCAAATAGCTGAAATGCAAACACTTCCAACAATCACTGATAAAACAGTTGTAT
erSerAlaGlnIleAlaGluMetGlnThrLeuProThrIleThrAspLysThrValValT

        250       260       270       280       290       300
ATTCCTGCAATAAACAAACGGTGACTGCTGTGTATCAATTTGAAAACCAAGAACCAGTTG
yrSerCysAsnLysGlnThrValThrAlaValTyrGlnPheGluAsnGlnGluProValA

        310       320       330       340       350       360
CTGCAATGGTAAGTGTGGGCGATGGCATTATTGCCAAAGATTTTACTCGTGATAAATCAC
laAlaMetValSerValGlyAspGlyIleIleAlaLysAspPheThrArgAspLysSerG

        370       380       390       400       410       420
AAAATGACTTTACAAGTTTCGTTTCTGGGGATTATGTTTGGAATGTAGATAGTGGCTTAA
lnAsnAspPheThrSerPheValSerGlyAspTyrValTrpAsnValAspSerGlyLeuT

        430       440       450       460       470       480
CGTTAGATAAATTTGATTCTGTTGTGCCTGTCAATTTAATTCAAAAAGGTAAATCTAGCG
hrLeuAspLysPheAspSerValValProValAsnLeuIleGlnLysGlyLysSerSerA

        490       500       510       520       530       540
ATAATATCATCGTCAAAAATTGTGATGTAAACGTAAAAGCAACTAAAAAAGCAAATTTAT
spAsnIleIleValLysAsnCysAspValAsnValLysAlaThrLysLysAlaAsnLeu*

        550       560       570       580       590       600
AATTAATCCCAAATGACCAGCATAATTGCTGGTTATTTATCTTCCTCGAGGGGAGATTTT
oc

        610       620       630       640       650       660
TTCTTGA
```

The sequence was found to have no significant homology to any known proteins including two previously described Haemophilus outer membrane lipoproteins of similar size.

The research described herein was supported in part by United States Public Health Service grant R01AI17572 from the National Institutes of Health.

[The sequence for the polynucleotide claimed in this application is as follows:

| SEQUENCE DESCRIPTION: SEQ ID NO: 1: | |
|---|---|
| GATCCCACCTTGTTTATTCCAATAATGGAACTTTATTTTATTAAAGGTATCTAAGTAGCA. | 60 |
| CCCTATATAGGGATTAATTAACGAGGTTTAATAATGAACTTTAACTAAAATTTTACCAGC | 120 |
| ATTTGCTGCTGTAGTCTGTATTATCTGCTTGTGCAAAGGATGCACCTGAAATGACAAAAT | 180 |
| CATCTGCGCAAATAGCTGAAATGCAAACACTTCCAACAATCACTGATAAAACAGTTGTAT | 240 |
| ATTCCTGCAATAAACAAACGGTGACTGCTGTGTATCAATTTGAAAACCAAGAACCAGTTG | 300 |
| CTGCAATGGTAAGTGTGGGCGATGGCATTATTGCCAAAGATTTTACTCGTGATAAATCAC | 360 |
| AAAATGACTTTACAAGTTTCGTTTCTGGGGATTATGTTTGGAATGTAGATAGTGGCTTAA | 420 |
| CGTTAGATAAATTTGATTCTGTTGTGCCTGTCAATTTAATTCAAAAAGGTAAATCTAGCG | 480 |
| ATAATATCATCGTCAAAAATTGTGATGTAAACGTAAAAGCAACTAAAAAAGCAAATTTAT | 540 |
| AATTAATCCCAAATGACCAGCATAATTGCTGGTTATTTATCTTCCTCGAGGGGAGATTTT | 600 |
| TTCTTGA | 607 |

The amino acid sequence for the outer membrane protein of haemophilus influenzae claimed in this application is as follows:

| SEQUENCE DESCRIPTION: SEQ ID NO: 2: |
|---|
| Met Thr Lys Ser Ser Ala Gln Ile Ala Glu Met Gln Thr Leu Pro Thr<br>1 5 10 15 |
| Ile Thr Asp Lys Thr Val Val Tyr Ser Cys Asn Lys Gln Thr Val Thr<br>20 25 30 |
| Ala Val Tyr Gln Phe Glu Asn Gln Glu Pro Val Ala Ala Met Val Ser<br>35 40 45 |
| Val Gly Asp Gly Ile Ile Ala Lys Asp Phe Thr Arg Asp Lys Ser Gln<br>50 55 60 |
| Asn Asp Phe Thr Ser Phe Val Ser Gly Asp Tyr Val Trp Asn Val Asp<br>65 70 75 80 |
| Ser Gly Leu Thr Leu Asp Lys Phe Asp Ser Val Val Pro Val Asn Leu<br>85 90 95 |
| Ile Gln Lys Gly Lys Ser Ser Asp Asn Ile Ile Val Lys Asn Cys Asp<br>100 105 110 |
| Val Asn Val Lys Ala Thr Lys Lys Ala Asn Leu<br>115 120 |

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
(A) LENGTH: 607 base pairs
(B) TYPE: nucleic acid
(C) STRANDEDNESS: single
(D) TOPOLOGY: linear -continued (ii) MOLECULE TYPE: DNA (genomic)

(iii) HYPOTHETICAL: NO (iv) ANTI-SENSE: NO (ix) FEATURE:
(A) NAME/KEY: misc_feature
(B) LOCATION: 171..539
(D) OTHER INFORMATION: /note="Nucleotides 171 through 539 encode the outer membrane protein of Haemophilus Influenzae of Sequence ID No. 2."

(xi) SEQUENCE DESCRIPTION: SEQ ID NO:1:

```
GATCCCACCT TGTTTATTCC AATAATGGAA CTTTATTTTA TTAAAGGTAT CTAAGTAGCA     60

CCCTATATAG GGATTAATTA ACGAGGTTTA ATAATGAACT TTAACTAAAA TTTTACCAGC    120

ATTTGCTGCT GTAGTCTGTA TTATCTGCTT GTGCAAAGGA TGCACCTGAA ATGACAAAAT    180

CATCTGCGCA AATAGCTGAA ATGCAAACAC TTCCAACAAT CACTGATAAA ACAGTTGTAT    240

ATTCCTGCAA TAAACAAACG GTGACTGCTG TGTATCAATT TGAAAACCAA GAACCAGTTG    300

CTGCAATGGT AAGTGTGGGC GATGGCATTA TTGCCAAAGA TTTTACTCGT GATAAATCAC    360

AAAATGACTT TACAAGTTTC GTTTCTGGGG ATTATGTTTG GAATGTAGAT AGTGGCTTAA    420

CGTTAGATAA ATTTGATTCT GTTGTGCCTG TCAATTTAAT TCAAAAAGGT AAATCTAGCG    480

ATAATATCAT CGTCAAAAAT TGTGATGTAA ACGTAAAAGC AACTAAAAAA GCAAATTTAT    540

AATTAATCCC AAATGACCAG CATAATTGCT GGTTATTTAT CTTCCTCGAG GGGAGATTTT    600

TTCTTGA                                                              607
```

(2) INFORMATION FOR SEQ ID NO:2:

(i) SEQUENCE CHARACTERISTICS:
(A) LENGTH: 123 amino acids
(B) TYPE: amino acid
(D) TOPOLOGY: linear (ii) MOLECULE TYPE: protein (iii) HYPOTHETICAL: NO (ix) FEATURE:
(A) NAME/KEY: misc_feature
(B) LOCATION: 1..123
(D) OTHER INFORMATION: /note="Nucleotides 171 through 539 encode the outer membrane protein of Haemophilus Influenzae of Sequence ID No. 2."

(xi) SEQUENCE DESCRIPTION: SEQ ID NO:2:

```
Met Thr Lys Ser Ser Ala Gln Ile Ala Glu Met Gln Thr Leu Pro Thr
  1               5                  10                  15

Ile Thr Asp Lys Thr Val Val Tyr Ser Cys Asn Lys Gln Thr Val Thr
             20                  25                  30

Ala Val Tyr Gln Phe Glu Asn Gln Glu Pro Val Ala Ala Met Val Ser
         35                  40                  45

Val Gly Asp Gly Ile Ile Ala Lys Asp Phe Thr Arg Asp Lys Ser Gln
     50                  55                  60

Asn Asp Phe Thr Ser Phe Val Ser Gly Asp Tyr Val Trp Asn Val Asp
 65                  70                  75                  80
```

-continued

```
Ser Gly Leu Thr Leu Asp Lys Phe Asp Ser Val Val Pro Val Asn Leu
                85                  90                  95

Ile Gln Lys Gly Lys Ser Ser Asp Asn Ile Ile Val Lys Asn Cys Asp
            100                 105                 110

Val Asn Val Lys Ala Thr Lys Lys Ala Asn Leu
        115                 120
```

]

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
(A) LENGTH: 607 base pairs
(B) TYPE: nucleic acid
(C) STRANDEDNESS: single
(D) TOPOLOGY: linear (ix) FEATURE:
(A) NAME/KEY: CDS
(B) LOCATION: 171..539

(xi) SEQUENCE DESCRIPTION: SEQ ID NO:1:

```
GATCCCACCT TGTTTATTCC AATAATGGAA CTTTATTTTA TTAAAGGTAT CTAAGTAGCA      60

CCCTATATAG GGATTAATTA ACGAGGTTTA ATAATGAACT TTAACTAAAA TTTTACCAGC     120

ATTTGCTGCT GTAGTCTGTA TTATCTGCTT GTGCAAAGGA TGCACCTGAA ATG ACA        176
                                                       Met Thr
                                                         1

AAA TCA TCT GCG CAA ATA GCT GAA ATG CAA ACA CTT CCA ACA ATC ACT       224
Lys Ser Ser Ala Gln Ile Ala Glu Met Gln Thr Leu Pro Thr Ile Thr
          5                  10                  15

GAT AAA ACA GTT GTA TAT TCC TGC AAT AAA CAA ACG GTG ACT GCT GTG       272
Asp Lys Thr Val Val Tyr Ser Cys Asn Lys Gln Thr Val Thr Ala Val
     20                  25                  30

TAT CAA TTT GAA AAC CAA GAA CCA GTT GCT GCA ATG GTA AGT GTG GGC       320
Tyr Gln Phe Glu Asn Gln Glu Pro Val Ala Ala Met Val Ser Val Gly
 35                  40                  45                  50

GAT GGC ATT ATT GCC AAA GAT TTT ACT CGT GAT AAA TCA CAA AAT GAC       368
Asp Gly Ile Ile Ala Lys Asp Phe Thr Arg Asp Lys Ser Gln Asn Asp
                 55                  60                  65

TTT ACA AGT TTC GTT TCT GGG GAT TAT GTT TGG AAT GTA GAT AGT GGC       416
Phe Thr Ser Phe Val Ser Gly Asp Tyr Val Trp Asn Val Asp Ser Gly
             70                  75                  80

TTA ACG TTA GAT AAA TTT GAT TCT GTT GTG CCT GTC AAT TTA ATT CAA       464
Leu Thr Leu Asp Lys Phe Asp Ser Val Val Pro Val Asn Leu Ile Gln
         85                  90                  95

AAA GGT AAA TCT AGC GAT AAT ATC ATC GTC AAA AAT TGT GAT GTA AAC       512
Lys Gly Lys Ser Ser Asp Asn Ile Ile Val Lys Asn Cys Asp Val Asn
    100                 105                 110

GTA AAA GCA ACT AAA AAA GCA AAT TTA TAATTAATCC CAAATGACCA             559
Val Lys Ala Thr Lys Lys Ala Asn Leu
115                 120
```

-continued

GCATAATTGC TGGTTATTTA TCTTCCTCGA GGGGAGATTT TTTCTTGA 607

(2) INFORMATION FOR SEQ ID NO:2:

(i) SEQUENCE CHARACTERISTICS:
(A) LENGTH: 123 amino acids
(B) TYPE: amino acid
(D) TOPOLOGY: linear (ii) MOLECULE TYPE: protein (xi) SEQUENCE DESCRIPTION: SEQ ID NO:2:

Met Thr Lys Ser Ser Ala Gln Ile Ala Glu Met Gln Thr Leu Pro Thr
1 5 10 15

Ile Thr Asp Lys Thr Val Val Tyr Ser Cys Asn Lys Gln Thr Val Thr
20 25 30

Ala Val Tyr Gln Phe Glu Asn Gln Glu Pro Val Ala Ala Met Val Ser
35 40 45

Val Gly Asp Gly Ile Ile Ala Lys Asp Phe Thr Arg Asp Lys Ser Gln
50 55 60

Asn Asp Phe Thr Ser Phe Val Ser Gly Asp Tyr Val Trp Asn Val Asp
65 70 75 80

Ser Gly Leu Thr Leu Asp Lys Phe Asp Ser Val Val Pro Val Asn Leu
85 90 95

Ile Gln Lys Gly Lys Ser Ser Asp Asn Ile Ile Val Lys Asn Cys Asp
100 105 110

Val Asn Val Lys Ala Thr Lys Lys Ala Asn Leu
115 120

(2) INFORMATION FOR SEQ ID NO:3:

(i) SEQUENCE CHARACTERISTICS:
(A) LENGTH: 369 base pairs
(B) TYPE: nucleic acid
(C) STRANDEDNESS: single
(D) TOPOLOGY: linear (xi) SEQUENCE DESCRIPTION: SEQ ID NO:3:

ATGACAAAAT CATCTGCGCA AATAGCTGAA ATGCAAACAC TTCCAACAAT CACTGATAAA 60

ACAGTTGTAT ATTCCTGCAA TAAACAAACG GTGACTGCTG TGTATCAATT TGAAAACCAA 120

GAACCAGTTG CTGCAATGGT AAGTGTGGGC GATGGCATTA TTGCCAAAGA TTTTACTCGT 180

GATAAATCAC AAAATGACTT TACAAGTTTC GTTTCTGGGG ATTATGTTTG GAATGTAGAT 240

AGTGGCTTAA CGTTAGATAA ATTTGATTCT GTTGTGCCTG TCAATTTAAT TCAAAAAGGT 300

AAATCTAGCG ATAATATCAT CGTCAAAAAT TGTGATGTAA ACGTAAAAGC AACTAAAAAA 360

GCAAATTTA 369

(2) INFORMATION FOR SEQ ID NO:4:

(i) SEQUENCE CHARACTERISTICS:
(A) LENGTH: 98 amino acids
(B) TYPE: amino acid
(C) STRANDEDNESS:
(D) TOPOLOGY: linear (xi) SEQUENCE DESCRIPTION: SEQ ID NO:4:

Cys Asn Lys Gln Thr Val Thr Ala Val Tyr Gln Phe Glu Asn Gln Glu
1 5 10 15

-continued

```
Pro Val Ala Ala Met Val Ser Val Gly Asp Gly Ile Ile Ala Lys Asp
            20                  25                  30

Phe Thr Arg Asp Lys Ser Gln Asn Asp Phe Thr Ser Phe Val Ser Gly
        35                  40                  45

Asp Tyr Val Trp Asn Val Asp Ser Gly Leu Thr Leu Asp Lys Phe Asp
    50                  55                  60

Ser Val Val Pro Val Asn Leu Ile Gln Lys Gly Lys Ser Ser Asp Asn
65                  70                  75                  80

Ile Ile Val Lys Asn Cys Asp Val Asn Val Lys Ala Thr Lys Lys Ala
                85                  90                  95

Asn Leu
```

We claim:

[1. The recombinant polynucleotide having the sequence

[

```
         10        20        30
GATCCCACCTTCTTTATTCCAATAATGGAA

                      CTTTATTTTATTAAAGGTATCTAAGTAGCA

CCCTATATAGGGATTAATTAACGAGGTFFA

                      ATAATGAACTTTAACTAAAATTTTACCAGC

ATTTGCTGCTGTAGTCTGTATTATCTGCTT

                      GTGCAAAGGATGCACCTGAaATGACAAAAT

CATCTGCGCAAATAGCTGAAATGCAAACAC
erSerAlaGlnIleAlaGluMetGlnThrL

                      TTCCAACAATCACTGATAAAACAGTTGTAT
                      euProThrIleThrAspLysThrValValT

ATTCCTGCAATAAACAAACGGTGACTGCTG
yrSerCysAsnLysGlnThrValThrAlaV

                      TGTATCAATTTGAAAACCAAGAACCAGTTG
                      alTyrGlnPheGluAsnGlnGluPrnValA

CTGCAATGGTAAGTGTGGGCGATGGCATTA
laAlaMetValSerValGlyAspGlyIleI

                      TTGCCAAAGATTTTACTCGTGATAAATCAC
                      leAlaLysAspPheThrArgAspLysSerG

AAAATGACTTTACAAGTTTCGTTTCTGGGG
InAsnAspPheThrSerPheValSerGlyA

                      ATTATGTTTGGAATGTAGATAGTGGCTTAA
                      spTyrValTrpAsnValAspSerGlyLeuT

CGTTAGATAAATTTGATTCTGTTGTGCCTG
hrLeuAspLysPheAspSerValValProV

                      TCAATTTAATTCAAAAAGGTAAATCTAGCG
                      alAsnLeuIleGlnLysGlyLysSerSerA

ATAATATCATCGTCAAAAATTGTGATGTAA
spAsnIleIleValLysAsnCysAspValA

                      ACGTAAAAGCAACTAAAAAAGCAAATTATT
                      snValLysAlaThrLysLysAlaAsnLeu*

AATTAATCCCAAATGACCAGCATAATTGCT
oc

                      GGTTATTTATCTTCCTCGAGGGGAGATTTT
```

-continued

```
      610     620     630     640     650     660
TTCTTGA (SEQ. ID. NO: 1)
```

]

encoding a polypeptide comprising immunoreactive epitopes of the 15 kD outer membrane protein of Haemophilus influenzae.]

[2. A vector comprising a recombinant polynucleotide, wherein the recombinant polynucleotide is the recombinant polynucleotide of claim 1.]

[3. A host cell transformed with the vector of claim 2.]

[4. A recombinant expression system comprising a polynucleotide encoding a polypeptide comprising one or more immunoreactive epitopes of the 15 kD outer membrane protein of claim 1, wherein the polynucleotide is operably linked to a control sequence compatible with a desired host.]

[5. A cell transformed with a recombinant expression system, wherein the expression system is the recombinant expression system of claim 4.]

*6. A recombinant polynucleotide encoding a polypeptide comprising the amino acid sequence of SEQ ID NO:2.*

*7. The recombinant polynucleotide of claim 6, comprising the nucleotide sequence of SEQ ID NO:3.*

*8. A recombinant polynucleotide encoding a polypeptide comprising the amino acid sequence of SEQ ID NO:4.*

*9. A recombinant vector comprising a recombinant polynucleotide encoding a polypeptide comprising the amino acid sequence of SEQ ID NO:2.*

*10. The recombinant vector of claim 9, wherein the recombinant polynucleotide comprises the nucleotide sequence of SEQ ID NO:3.*

*11. A recombinant vector comprising a recombinant polynucleotide encoding a polypeptide comprising the amino acid sequence of SEQ ID NO:4.*

*12. A host cell transformed with a vector comprising a recombinant polynucleotide encoding a polypeptide comprising the amino acid sequence of SEQ ID NO:2.*

*13. The host cell of claim 12, wherein the recombinant polynucleotide comprises the nucleotide sequence of SEQ ID NO:3.*

*14. A host cell transformed with a vector comprising a recombinant polynucleotide encoding a polypeptide comprising the amino acid sequence of SEQ ID NO:4.*

*15. A recombinant expression system comprising a recombinant polynucleotide encoding a polypeptide comprising the amino acid sequence of SEQ ID NO:2 operably linked to a control sequence compatible with a desired host.*

*16. The recombinant expression system of claim 15, wherein the recombinant polynucleotide comprises the nucleotide sequence of SEQ ID NO:3.*

*17. A recombinant expression system comprising a recombinant polynucleotide encoding a polypeptide comprising the amino acid sequence of SEQ ID NO:4 operably linked to a control sequence compatible with a desired host.*

*18. A cell transformed with a recombinant polynucleotide encoding a polypeptide comprising the amino acid sequence of SEQ ID NO:2.*

*19. The cell of claim 18, wherein the recombinant polynucleotide comprises the nucleotide sequence of SEQ ID NO:3.*

*20. A cell transformed with a recombinant polynucleotide encoding a polypeptide comprising the amino acid sequence of SEQ ID NO:4.*

*21. A method of making a recombinant vector capable of expressing a polypeptide comprising the amino acid sequence of SEQ ID NO:2, comprising*

*inserting a recombinant polynucleotide encoding a polypeptide comprising the amino acid sequence of SEQ ID NO:2 into a plasmid.*

*22. The method of claim 21, wherein the polynucleotide comprises the nucleotide sequence of SEQ ID NO:3.*

*23. A method of making a recombinant vector capable of expressing a polypeptide comprising the amino acid sequence of SEQ ID NO:4, comprising*

*inserting a recombinant polynucleotide encoding a polypeptide comprising the amino acid sequence of SEQ ID NO:4 into a plasmid.*

*24. A method of making a polypeptide comprising the amino acid sequence of SEQ ID NO:2, comprising*

*culturing a host cell transformed with a recombinant vector comprising a recombinant polynucleotide encoding a polypeptide comprising the amino acid sequence of SEQ ID NO:2, whereby the host cell expresses the polypeptide, and*

*isolating the polypeptide.*

*25. The method of claim 24, wherein the polynucleotide comprises the nucleotide sequence of SEQ ID NO:3.*

*26. A method of making a polypeptide comprising the amino acid sequence of SEQ ID NO:4, comprising*

*culturing a host cell transformed with a recombinant vector comprising a recombinant polynucleotide encoding a polypeptide comprising the amino acid sequence of SEQ ID NO:4, whereby the host cell expresses the polypeptide, and*

*isolating the polypeptide.*

* * * * *